(12) United States Patent
Nørgaard

(10) Patent No.: US 9,986,940 B2
(45) Date of Patent: Jun. 5, 2018

(54) MICROPHONE CALIBRATION COMPENSATION FROM COUPLER TRANSFER FUNCTION

(71) Applicant: Interacoustics A/S, Middelfart (DK)

(72) Inventor: Kren Rahbek Nørgaard, Smørum (DK)

(73) Assignee: INTERACOUSTICS A/S, Middelfart (DK)

( * ) Notice: Subject to any disclaimer, the term of this patent is extended or adjusted under 35 U.S.C. 154(b) by 0 days. days.

(21) Appl. No.: 15/493,359

(22) Filed: Apr. 21, 2017

(65) Prior Publication Data
US 2017/0311850 A1 Nov. 2, 2017

(30) Foreign Application Priority Data

Apr. 29, 2016 (EP) ..................................... 16167706

(51) Int. Cl.
*H04R 29/00* (2006.01)
*A61B 5/12* (2006.01)
*H04R 3/04* (2006.01)

(52) U.S. Cl.
CPC ............... *A61B 5/125* (2013.01); *H04R 3/04* (2013.01); *H04R 29/004* (2013.01); *A61B 2560/0223* (2013.01); *A61B 2560/0431* (2013.01)

(58) Field of Classification Search
CPC .... H04R 29/00; H04R 29/004; H04R 29/005; H04R 29/006; H04R 3/04; H04R 3/10; A61B 5/12; A61B 5/121; A61B 5/123; A61B 5/125; A61B 2560/0223
USPC ......... 381/58, 60, 91, 92, 122, 95, 312, 313; 600/559; 73/585
See application file for complete search history.

(56) References Cited

U.S. PATENT DOCUMENTS

| 5,651,371 A | 7/1997 | Keefe | |
|---|---|---|---|
| 7,548,625 B2 * | 6/2009 | Dorfman | H04R 29/001 381/58 |
| 7,961,891 B2 * | 6/2011 | Dorfman | H04R 29/001 381/122 |
| 8,839,657 B2 * | 9/2014 | Siegel | G01N 29/30 73/1.82 |

(Continued)

FOREIGN PATENT DOCUMENTS

| JP | 1-217216 A | 8/1989 |
|---|---|---|
| SU | 623273 A1 | 9/1978 |

OTHER PUBLICATIONS

Rasetshwane et al., "Calibration of otoacoustic emission probe microphones", The Journal of the Acoustical Society of America, American Institute of Physics for the Acoustical Society of America, New York, US, vol. 130, No. 4, pp. EL238-EL243.

*Primary Examiner* — Xu Mei
(74) *Attorney, Agent, or Firm* — Birch, Stewart, Kolasch & Birch, LLP

(57) ABSTRACT

The present disclosure relates to a method and system for determining the sensitivity of a first microphone, the method comprising providing an acoustic coupler having at least one internal cavity configured such that a sound field can be generated within the cavity, the cavity being further in acoustic communication with a reference microphone configured to measure the reference sound pressure at a given position in said cavity, the cavity being further provided with an inlet opening configured to establish acoustic communication between the sound inlet of said first microphone, the sensitivity of which is to be determined.

20 Claims, 9 Drawing Sheets

(56) References Cited

U.S. PATENT DOCUMENTS

| | | | |
|---|---|---|---|
| 2004/0037428 A1* | 2/2004 | Keller | A61B 5/121 381/60 |
| 2007/0112279 A1 | 5/2007 | Iseberg et al. | |
| 2014/0079228 A1 | 3/2014 | Doller | |
| 2016/0366526 A1* | 12/2016 | Norgaard | A61B 5/12 |
| 2016/0381456 A1* | 12/2016 | Doller | H04R 29/004 381/113 |

* cited by examiner

MICROPHONE CALIBRATION COMPENSATION FROM COUPLER TRANSFER FUNCTION

FIELD

The present disclosure relates generally to determining the sensitivity of a microphone as a function of frequency and more specifically to determining the sensitivity of a microphone in an acoustic unit, such as an acoustic probe, used for instance in hearing diagnostics.

BACKGROUND

Some modalities in hearing diagnostics involve the measurement of sound pressure in the ear canal. Measuring a correct sound pressure in the first place is also the foundation for estimating other related quantities, e.g., the sound pressure at the tympanic membrane, acoustic intensity, or sound power transmitted to the inner ear.

Modalities in hearing diagnostics involving the measurement of sound pressure in the ear canal include among others otoacoustic emissions (OAE). In OAE measurements, a sound produced by well-functioning hair cells in the cochlea that is loud enough to be recorded by a microphone positioned in the ear canal of a patient (i.e., a test-subject) is measured. The OAE measurements may provide relevant information of a patient's hearing capabilities and may assist in identifying damage of the ear canal potentially providing indication of a hearing loss. Especially, OAE measurements are useful when testing infants and/or younger children.

For assisting in the recording of OAEs in the ear canal, a diagnostic tool, configured to provide objective information of different pathologies of the ear by use of a series of measurements, is used. In more detail, such diagnostic tool comprises a handle element and an acoustic unit, such as a probe unit configured to create stimuli and/or sound signals in the ear canal of, e.g., a human test-subject. The probe unit generally consists of at least one output unit, such as a receiver and a sound input unit, such as a microphone. In addition, such diagnostic tool may further comprise a pressure unit configured to cause a changing pressure in the ear canal of a test-subject, such as in pressurized OAE measurements. The probe unit as such is an element, which is configured to output stimuli signals for provoking an ear canal response, where the input unit, such as a microphone, measures ear-canal responses.

Thus, when performing diagnostic measurements related to measuring an accurate sound pressure in the ear canal, it is important that the input sound unit (e.g., a microphone) records the most accurate and correct measurements as possible. One factor that may influence such recording is the sensitivity of the microphones used in probe units, and it is therefore of importance to know the sensitivity of the microphone, when evaluating different diagnostic measurements.

The microphones used for probes (i.e., probe units) in hearing diagnostics are mostly of a commercial type (same as in hearing aids) where variations in sensitivity across the frequency spectrum is to be expected. Furthermore, there are often differences between the sensitivity of different microphones of the same type used in different probes. Such microphones can therefore not be assumed to have a flat frequency response. It should be noted that reference microphones used for calibration of the sensitivity of probe microphones as for instance described in the following do normally not suffer from such problems. Accordingly, for obtaining the most accurate response from the ear canal when exposed to a stimulus and recorded by a probe microphone, a calibration is often carried out to obtain the complex probe microphone sensitivity that relates the voltage output from the microphone to the sound pressure at the tip of the probe unit.

Currently, the most precise way to obtain the probe microphone sensitivity is by placing the probe microphone in an acoustic free-field next to a reference microphone and thereby assuming that the two microphones are subject to the same sound pressure. This is a rather extensive measurement since it, preferably, requires an anechoic chamber or a sound box, is quite sensitive to noise and not very convenient in the context of a calibration procedure for a diagnostic probe.

A more simple method is to insert the probe in a small coupler (e.g., the commercially available G.R.A.S. 0.4 cc coupler) and assuming that the sound pressure at the probe microphone and a reference microphone of the coupler is equivalent. This is, however, not the case towards higher frequencies due to standing waves in the cavity and the probe being inserted opposite to the reference microphone. The result of these standing waves is a large error towards the ¼-wavelength resonance of the coupler since the sound pressure at the probe cancels out. A rough sketch of such setup is depicted in FIG. 1.

To reduce the effect of this cancellation (i.e., the error caused by standing waves), one option is to reduce the size of the coupler thereby transitioning the notch (i.e., the error) towards higher frequencies. This has been tested using a special insert in the 0.4 cc coupler reducing the volume to approximately 0.13 cc. This transitioned the notch to approximately 17 kHz, but significant errors were still present due to impedance mismatch towards the notch. Smaller cavities are not feasible due to limitations in the physical size of the reference microphone.

Rasetshwane and Neely [2] describe a method in which a probe-tube microphone is initially calibrated at the end of a waveguide using a reference microphone. The probe for which the microphone sensitivity is to be found then replaces the reference microphone and the probe-tube microphone is now used as the reference microphone. This procedure is, however, also quite extensive since it besides the reference microphone also requires an additional external microphone and sound source.

Hence, there exists a need for a microphone calibration method that makes it possible to obtain the sensitivity of a microphone, such as a probe microphone used for instance in hearing diagnostics, over a very wide frequency range without the need of an acoustic free-field measurement or any external transducers other than a reference microphone. There further exists a need for a microphone calibration method that does not require a coupler or similar device, the physical dimensions of which are not so small that it poses a problem due to limitations of the size of the reference microphone.

SUMMARY

Accordingly, the above and further objects and advantages are obtained by a microphone calibration method according to the present disclosure, the method generally being based on the capability of measuring the acoustic impedance of an acoustic coupler unit and estimating the acoustic transfer impedance of the acoustic coupler across the frequency spectrum in which an acoustic unit sensitivity is desired, such as the probe unit microphone sensitivity. The method and aspect thereof according to the disclosure will become apparent in the following description.

In the following, whenever reference is made to a an "acoustic unit", "probe" or equally a "probe unit", the probe may comprise at least one microphone and one speaker configured to generate a suitable sound signal and/or stimulus signal that can be used inter alia for probe-unit calibration purposes.

Similarly, in the following, whenever reference is made to an "acoustic coupler" or equally a "coupler unit" or "coupler", it should be understood that this refers to substantially the same "unit" and that said coupler may comprise at least one reference microphone for calibration purposes.

Specifically, the probe unit itself can be calibrated in a previous step (c.f. for instance [1]) to obtain its Thevenin source parameters, which allows the probe to measure any acoustic load it is subjected to. For more details on the Thevenin parameter calibration of the probe unit, please refer to reference [1].

Furthermore, when referring to the "input unit" of the acoustic unit should be contemplated as a "unit", which is configured to at least record a transmitted signal as a response to an acoustic stimulus in an enclosure. Thus, the "input unit" is preferably a microphone as is apparent from the description.

According to the embodiments of the present disclosure it may be that the speaker (i.e., the sound source), which is used for stimulating during the microphone-sensitivity measurement, is also the one used for the impedance measurement of the acoustic coupler. This means that the transition effects between the probe and the acoustic coupler (that primarily affect the impedance minima) are the same in the sensitivity and impedance measurements and can therefore be compensated perfectly, given the transfer impedance of the acoustic coupler (these quantities are defined in detail in the following). There are no impedance minima in the transfer impedance of the acoustic coupler, and since the reference microphone of the acoustic coupler measures sound pressure almost across the entire end plane of the acoustic coupler, it is therefore not affected by these effects, and the transfer impedance of the acoustic coupler can be calculated analytically.

According to an embodiment, the input impedance of the acoustic coupler and the probe microphone sensitivity may be measured simultaneously and not in two separate steps, with the stimulating sound source being the one whose Thevenin parameters have been determined previously.

However, according to an embodiment, these quantities (i.e., the input impedance of the coupler and the probe-microphone sensitivity) may also be measured separately, such as in two different steps of a calibration procedure.

According to a first aspect of the present disclosure there is provided a method for determining the sensitivity of a microphone in an acoustic unit (such as a probe unit), the method comprising;
  providing an acoustic unit, such as a probe unit used for diagnostic purposes;
  providing an acoustic coupler having at least one internal cavity configured such that a sound field can be generated within the cavity. The cavity is further in acoustic communication with a reference microphone, the reference microphone being configured to measure a reference sound pressure at a given position in the cavity;
  establishing an acoustic communication between the acoustic coupler and the acoustic unit. This being achieved by the cavity being further provided with an inlet opening configured to establish acoustic communication between the sound inlet of the acoustic unit, the sensitivity of which is to be determined;
  determining the sensitivity of the acoustic unit, wherein the sensitivity of the acoustic unit is determined as the ratio between the output voltage V(f) of the acoustic unit and a reference sound pressure $p_{ref}$ generated in the cavity by a sound source (e.g., a receiver) and measured by the reference microphone multiplied by a frequency-dependent transfer-function, where the transfer function is a function of the input impedance $Z_{in}$ at the inlet opening of the acoustic coupler and the transfer impedance $Z_{trans}$ between the inlet opening of the acoustic coupler and the position at which the reference sound pressure $p_{re}$ is being measured by the reference microphone.

By this method, the sensitivity of the acoustic unit (i.e., the probe microphone) can be calculated and compensated for in a calibration step, whereby more accurate measurements of the sound pressure in the ear canal may be achieved. This method uses an analytical representation of an acoustic transfer impedance and the acoustic input impedance of the acoustic coupler (used for calibration purposes) to estimate the sensitivity of the input unit, i.e., the probe microphone used for recording the sound pressure in the ear canal.

When referring to "compensated sensitivity" or "sensitivity" in should be understood as the actual sensitivity of the acoustic unit, whereas "non-compensated sensitivity" refers to the actual sensitivity including the errors arising from the resonances in the acoustic coupler.

In an embodiment, the input impedance $Z_{in}$ at the inlet opening of the acoustic coupler may be predetermined or measured.

In an embodiment, the transfer-function may be directly predetermined, e.g., from a transmission line model.

In an embodiment, the acoustic unit comprises a microphone unit, the sensitivity of which is to be measured and compensated for, and a sound source (e.g., a speaker or equally a receiver unit) configured to generate a sound field and/or stimulus in the acoustic coupler, when the acoustic unit is in acoustic communication with the acoustic coupler.

In an embodiment, the sound source generating a sound field and/or stimuli in the acoustic coupler for measuring the sensitivity of the acoustic unit is also the sound source that is used for the input impedance measurement. With this configuration of the method it is achieved that the transition effects between the probe and the acoustic coupler (that primarily affect the impedance minima) are the same in the sensitivity and impedance measurements and these transition effects can therefore be compensated perfectly or substantially perfectly given the transfer impedance.

In an embodiment, the transfer impedance $Z_{trans}$ of the acoustic coupler is determined analytically in relation to the specific acoustic coupler being used for measuring the sensitivity or measured using other equipment than the acoustic unit.

In an embodiment, the transfer impedance is calculated analytically based on the physical dimensions of the acoustic coupler, e.g., from a transmission-line model given by:

$$\begin{pmatrix} p_{ref} \\ U_{ref} \end{pmatrix} = \begin{pmatrix} \cosh(\Gamma L) & -Z_0 \sinh(\Gamma L) \\ -\frac{1}{Z_0}\sinh(\Gamma L) & \cosh(\Gamma L) \end{pmatrix} \cdot \begin{pmatrix} p_{probe} \\ U_{probe} \end{pmatrix}$$

where $Z_0$ is the characteristic impedance, $\Gamma$ is the propagation constant, L is the length of the transmission line, $p_{ref}$ is the pressure on the reference microphone of the coupler, $U_{ref}$ is the volume velocity injected into the reference microphone, $p_{probe}$ is the pressure on the acoustic unit (i.e., the microphone unit of the probe unit) and $U_{probe}$ is the volume velocity injected into the coupler by the acoustic unit.

In an embodiment, the acoustic coupler may be a commercially available G.R.A.S. 0.4 cc (cubic centimeter) coupler.

However, it should be noted that other suitable acoustic couplers and/or waveguides, for which the transfer-function can be found are suitable for use with the method described herein. The 0.4 cc acoustic coupler merely indicates an example of use, and it would be apparent for a skilled person that other acoustic couplers could equally be used, as long as the transfer-function for these couplers can be calculated and/or measured. In principle, any acoustic enclosure for which the transfer-function, acoustic input impedance and/or acoustic transfer impedance can be measured and/or modeled can be utilized for this method.

In an embodiment, the acoustic unit may be part of an acoustic probe configured for use inter alia in hearing diagnostics.

According to a second aspect of the disclosure, a diagnostic tool for performing hearing diagnostics is provided for. The hearing-diagnostic tool is configured to perform hearing diagnostics and to perform a calibration procedure according to the method described herein.

Accordingly, in an embodiment, the diagnostic tool comprises a handle element having a first end and a second end, wherein an acoustic unit is provided in the second end. Furthermore, the acoustic unit may comprise at least one output unit configured to provide a stimuli signal to an acoustic coupler and/or an ear canal of a test-subject, and at least one input unit configured to record a transmitted sound from inside, e.g., the acoustic coupler and/or an ear canal of a test-subject, wherein the diagnostic tool further comprises a processing unit, the processing unit being configured to perform a calibration procedure of the acoustic unit, the calibration procedure being performed as described in relation to the method according to embodiments of the disclosure.

In an embodiment of the second aspect, the acoustic unit, such as a probe unit, is connected to the diagnostic tool, such as the second end of the handle element, by use of a communication element configured to transmit information to and/or from part of the acoustic unit. By partly creating a physical spacing between the acoustic unit and the handle element, potential vibrations or other motional effects introduced by an "operator" or similarly a "user" (e.g., a hearing care professional) is avoided. Such introduced vibration and/or motional effects from operating the diagnostic tool might lead to the introduction of errors in the measurements performed by the acoustic unit and such errors should preferably be limited as much as possible.

Thus in an embodiment, the acoustic unit may comprise the acoustical elements, such as the input unit (i.e., the microphone) in one end configured to be inserted into the ear canal and/or an acoustic coupler and a second connection end configured to attach the acoustic unit to the diagnostic tool, wherein the acoustical elements are connected to the connection end by for example the communication element. The communication element, configured to transmit information, may be one or more electrically leading cables and/or wires, which preferably are separated from the environment by an enclosure, such as a tubing.

In an embodiment, it may be that the communication between the acoustic unit, such as the acoustic elements of the acoustic unit and the diagnostic tool is achieved by a wireless connection.

In an embodiment, it may be that the data obtained from the calibration procedure are saved in the acoustic unit, rather than the diagnostic tool as such. In this way, the acoustic unit may be interchangeable between different diagnostic tools.

With a diagnostic tool of this type, the calibration of acoustic units, such as probe microphones in a probe unit, may easily be done, while avoiding the need for extensive acoustic free-field setups, limitation problems and extensive calibration procedures due to limitation on coupler sizes as described previously. With this method, the diagnostic tool may be configured to perform the calibration procedure directly with at least an acoustic coupler and thus the method provides a more easy calibration setup to be applied during for example hearing diagnostics.

In an embodiment, the diagnostic tool may further comprise a pressure unit configured to cause a changing pressure in the ear canal of a test-subject.

It should be noted, that the configuration of the processing unit of the diagnostic tool will be described in more detail in relation to a hearing diagnostic system according to the disclosure. Thus, features of the aspect described herein should be understood to be equally included in the aspects for which they are not directly described, but for which it would be apparent for a person skilled in the art to include.

According to a third aspect of the disclosure, a system for providing hearing diagnostics is provided for. The system comprises:
an acoustic coupler,
a diagnostic tool configured to perform hearing diagnostics, the diagnostic tool comprising;
a handle element having a first end and a second end, wherein an acoustic unit is provided in the second end;
the acoustic unit comprising at least one output unit configured to provide a stimulus signal to the acoustic coupler, and at least one input unit configured to record a transmitted sound from inside said acoustic coupler, the diagnostic tool further comprising a processing unit, the processing unit being configured to perform a calibration procedure of the acoustic unit when the diagnostic tool is in acoustic communication with a cavity of the acoustic coupler during calibration procedures, wherein the calibration procedure is carried out in accordance with the method described in the first aspect.

In an embodiment of the third aspect, the processing unit includes a microphone calibration setup, configured to calibrate the microphone in the acoustic unit in accordance with the method according to the first aspect.

In an embodiment of the aspects, the output unit of the acoustic unit is a speaker unit configured to emit an acoustic stimulus and/or sound signal into said acoustic coupler, and said input unit is a microphone unit configured to measure the resulting sound pressure at an inlet position of the acoustic coupler, wherein said acoustic coupler further comprises a reference microphone configured to measure the sound pressure at an outlet position of said acoustic coupler.

In an embodiment, the processing unit is configured to provide an electrical signal to the sound source, whereby the sound source emits the acoustic stimuli and/or sound signal into the acoustic coupler, the processing unit being further configured to receive an electrical output signal from the reference microphone of the acoustic coupler; and store data comprising acoustic parameters characterizing the acoustic behavior of the acoustic coupler.

Furthermore, in an embodiment, the calibration procedure and/or calibration setup is configured to calibrate a microphone unit of the acoustic unit, at least by use of the method of the first aspect. That is, the calibration procedure is configured to perform the method according to the first aspect in order to calibrate the sensitivity of the microphone such that more accurate measurements during hearing diagnostic measurements is achieved.

In an embodiment of the aspects described herein, the acoustic parameters characterizing the acoustic behavior of the coupler comprises the input impedance, $Z_{in}$ of the acoustic coupler where the input impedance is predetermined or measured, and/or wherein stored values of the processing unit comprises any members of the following group or any combinations of these members: recordings or analytical measurements of the system includes; the output voltage provided by the acoustic unit (such as a probe), the sound pressure measured by the reference microphone, the calculated analytical or predetermined transfer impedance of the acoustic coupler.

In an embodiment, the processing unit is configured to calculate the analytical transfer impedance of the acoustic coupler from said stored data and further to output and/or store the calculated compensated microphone sensitivity value(s) for a specific frequency range.

The system according to the third aspect may similarly be configured to calculate the sensitivity of the microphone in the acoustic unit for the purpose of performing a microphone calibration procedure, wherein the sensitivity of the microphone is estimated from an acoustic transfer-function of the acoustic coupler.

Accordingly, the processing unit of the system may be configured to calculate and output a compensated microphone sensitivity (i.e., the sensitivity of the microphone) in accordance with the method of the first aspect.

In an embodiment of the aspects of the system, a diagnostic tool and/or method is configured to apply alternative different couplers, which would be apparent for a person skilled in the art to use when applying the method as described herein.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of non-limiting example embodiments of the aspects, including the method, diagnostic tool, and diagnostic hearing system, according to the present disclosure.

Figure 1:
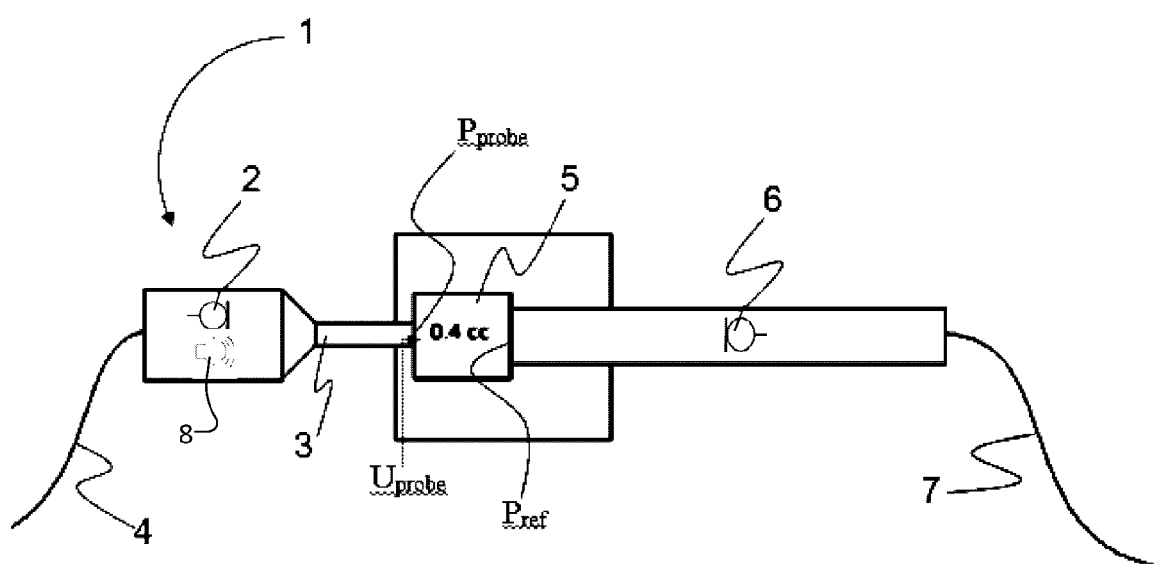
FIG. 1 shows a schematic illustration of a microphone calibration setup applying a 0.4 cc coupler, a reference microphone and a suitable sound source configured to create a sound field in the coupler (the sound source is not shown in the figure since the probe consists of at least a sound source and a microphone ([c.f. for instance reference [1])

With reference to FIG. 1 there is shown a schematic illustration of a microphone-calibration setup applying a 0.4 cc coupler, a reference microphone and a suitable sound source configured to create a sound field in the coupler (the sound source is not shown in the figure since the probe consists of at least a sound source and a microphone, c.f. for instance reference [1]) This setup constitutes a non-limiting example of a setup that can be used to implement the method according to the present disclosure.

FIG. 1 shows a probe unit (i.e., equally an acoustic unit) generally designated by reference numeral 1 and comprising a probe microphone 2 and a sound source 8. Furthermore, a sound tubing 3 is illustrated and configured to provide acoustic communication between a sound field (in this example existing in the acoustic coupler 5) and a diaphragm of the microphone contained in the probe unit 1. It should be noted that the setup illustrated in FIG. 1 is only one example of how to setup a calibration procedure according to the method herein. Thus, the shown arrangement of, e.g., the probe microphone 2 and the sound source (e.g., a speaker unit) 8 is only for illustrative purposes. It should be noted that the sound tubing 3 preferably comprises one or more acoustical "pipes", "channels" and/or "sound-guiding cavities" (not shown), at least one sound guiding cavity being in communication with the microphone and one sound guiding cavity being in communication with the receiver.

The sound signal provided through the sound tubing 3 is recorded and converted to an electrical output signal by the probe microphone 2 in the acoustic unit 1 and transmitted through line 4 to a processing unit for further processing. Also acoustically connected to the coupler 5 there is provided the reference microphone 6 which provides the electrical output signal 7, when the diaphragm of the reference microphone 6 is subjected to a sound pressure, i.e., the sound pressure in the coupler 5 in the setup shown in FIG. 1. The processing of the recorded signals transmitted through lines 4 and 7 to a processing unit will become apparent throughout the description.

Also indicated in FIG. 1 are the sound pressure $p_{probe}$ at the entrance of the sound tube 3 of the probe microphone 2 and the corresponding volume velocity $U_{probe}$. The sound pressure at the diaphragm of the reference microphone 6 is designated by $p_{ref}$ in FIG. 1. The various quantities indicated in FIG. 1 will be referred to in the following detailed description of an embodiment of the present disclosure.

The principles of the present disclosure are based on the capability of measuring the acoustic input impedance of the acoustic coupler and estimating the acoustic transfer impedance across the frequency spectrum in which the microphone sensitivity is desired. Specifically, impedance measurements in the examples presented in this invention disclosure are based on a Thevenin calibration of a probe as described in [1]. Assuming that the sound pressure at the reference microphone and the probe microphone is equivalent, the microphone non-compensated sensitivity is calculated by dividing the voltage measured from the probe microphone by the sound pressure on the reference microphone:

$$\text{Sensitivity} = \frac{V_{probe}}{p_{ref}}$$

The sound stimulus is delivered by one or more speakers (i.e., the sound source) in the acoustic unit (i.e., the probe).

However, as mentioned in the background of the disclosure, it cannot be assumed that the sound pressure at the probe microphone is the same as at the reference microphone. Hence, if the above expression is applied to calculate the microphone sensitivity, errors will be introduced that are particularly dominant at higher frequencies. This is illustrated in FIGS. 2A and 2B.

Figure 2A:
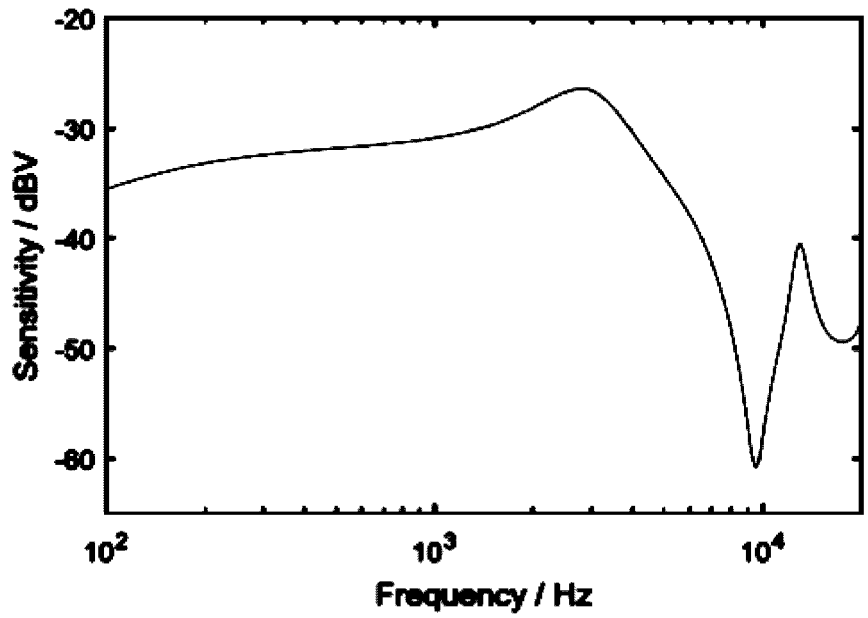
FIG. 2A and FIG. 2B show plots of the magnitude (FIG. 2A) and phase (FIG. 2B) of the sensitivity of a diagnostic probe microphone obtained by means of a G.R.A.S. 0.4 cc coupler without further compensation.
Figure 2B:
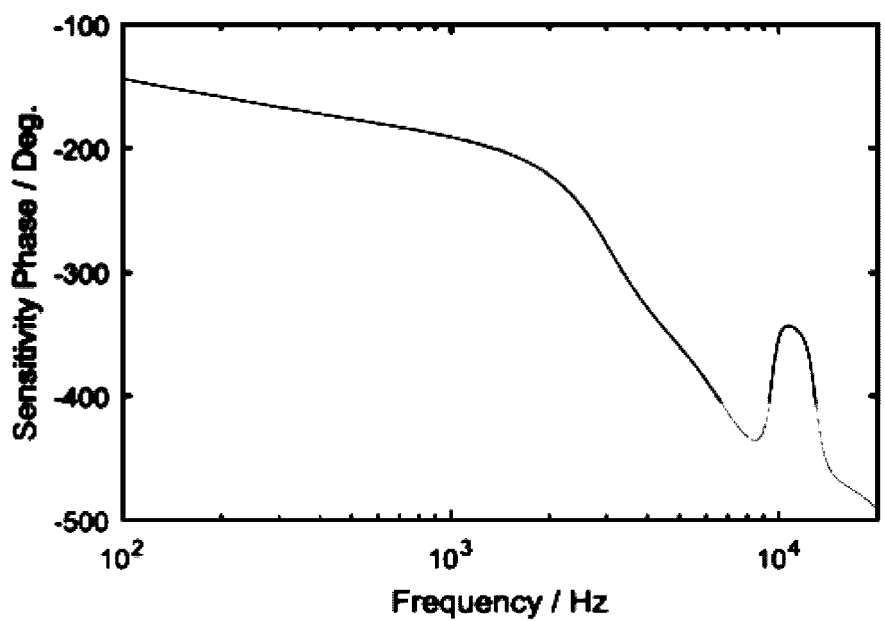

With reference to FIGS. 2A and 2B there are shown plots of the magnitude (FIG. 2A) and phase (FIG. 2B) of the sensitivity of a diagnostic probe microphone obtained by means of a G.R.A.S. 0.4 cc coupler without further compensation. As is seen from FIGS. 2A and 2B, both the magnitude and phase of the sensitivity measurement show a large notch 8 around 9.5 kHz. The large notch 8 at approximately 9.5 kHz is a result of the ¼ standing wave in the coupler and induces a huge error in the obtained sensitivity.

The assumption during prior art measurement of sensitivity using a setup as shown in FIG. 1 is that the sound pressure throughout the coupler is uniform. This is equivalent to approximating the coupler as a capacitor in a lumped element analogy with an acoustic impedance given by $$Z_c = \frac{\rho c^2}{i \omega V}$$

As mentioned above, the Thevenin parameters of the probe were and equally may be obtained prior to the measurement of the microphone sensitivity. The input impedance $Z_{in}$ of the acoustic coupler is thus determined prior to the measurement of the probe-microphone sensitivity. The complex value of the input impedance $Z_{in}$ is for instance stored for subsequent use in, e.g., a memory of a processing unit in the equipment (e.g., a hearing-diagnostic tool), used to measure the probe microphone sensitivity. Alternatively, the input impedance could be measured simultaneously with the microphone sensitivity.

Figure 3A:
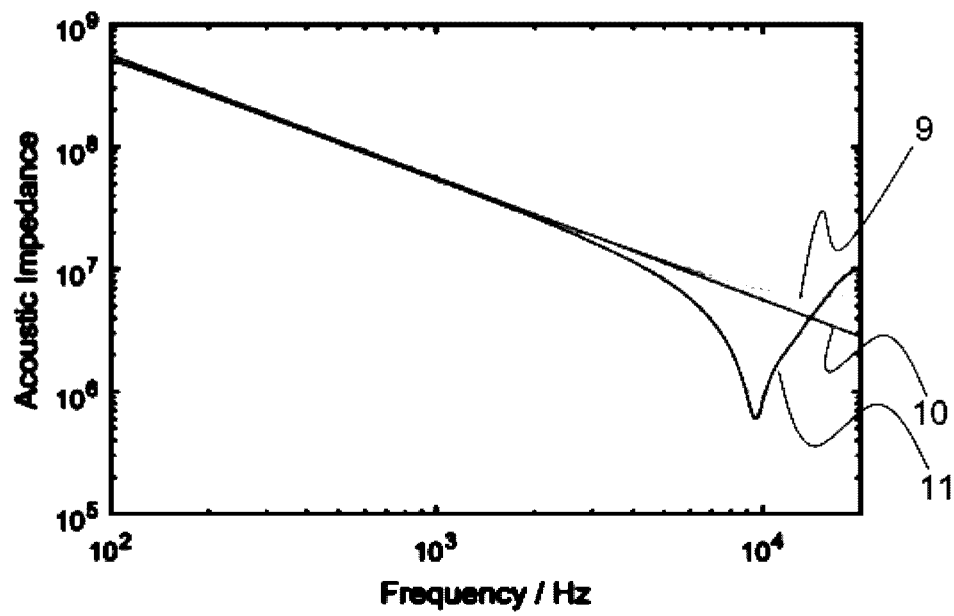
FIG. 3A and FIG. 3B show plots of the magnitude (FIG. 3A) and phase (FIG. 3B) of the measured input impedance, analytically determined lumped element input impedance and analytically determined transfer impedance of the G.R.A.S. 0.4 cc coupler.
Figure 3B:
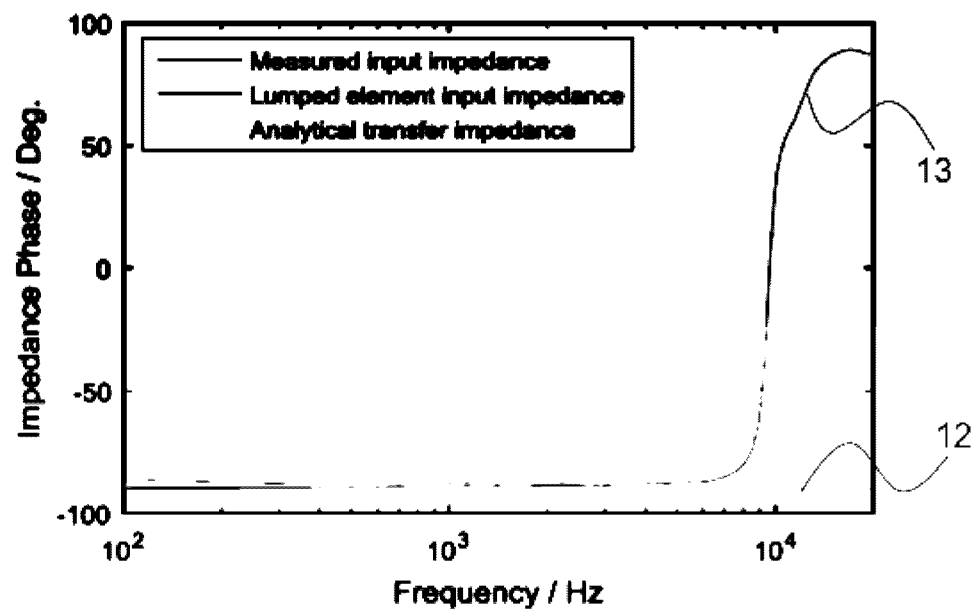

With reference to FIGS. 3A and 3B there are shown the magnitude (FIG. 3A) and phase (FIG. 3B) of the acoustic coupler input impedance 11 and 13 obtained through the Thevenin calibration of the probe unit and the corresponding lumped-element approximation 10 and 12 given by the expression for $Z_c$ above. FIGS. 3A and 3B further show the analytically determined transfer impedance 9 (the phase plot is practically coincident with 12) for the acoustic coupler used and the analytically determined transfer impedance to be explained in the following. The figures indicate that huge errors in the sensitivity towards higher frequencies are to be expected.

The measured acoustic input impedance 11, 13 is affected by numerous acoustical effects since it is measured as seen from the probe (this is the main idea behind the method disclosed in [1]). This means that the sound pressure on the probe microphone is during sensitivity calibration also affected by these effects when stimulating with the speaker that was used during the Thevenin calibration. These effects include evanescent modes and spreading flow losses and are described more in detain in [1]. These effects are localized effects within the acoustic coupler and are only present in close proximity to the sound outlet. Even though the evanescent modes may have not decayed entirely towards the end of the coupler, they do not affect the transfer impedance since the reference microphone measures the sound pressure across the entire surface of the coupler end. These acoustical effects can therefore be neglected in the transfer impedance of the acoustic coupler, being defined as the pressure, $p_{ref}$, on the reference microphone divided by the volume velocity, $U_{probe}$, injected in the opposite end of the coupler by the probe (the transfer impedance might have a different definition in other parts of the literature):

$$Z_{trans} = \frac{p_{ref}}{U_{probe}}$$

With the input impedance of the acoustic coupler defined as the pressure, $p_{probe}$, on the probe microphone divided by the volume velocity, $U_{probe}$, injected in the opposite end of the coupler by the probe:

$$Z_{in} = \frac{p_{probe}}{U_{probe}}$$

The ratio between the sound pressure present at the reference microphone and at the probe microphone can be calculated as follows:

$$\frac{Z_{trans}}{Z_{in}} = \frac{p_{ref}}{p_{probe}} \rightarrow p_{probe} = p_{ref} \frac{Z_{in}}{Z_{trans}}$$

In this way, the actual pressure on the probe microphone can be calculated in terms of the acoustic impedance seen from the probe and the acoustic transfer impedance. The transfer impedance can be calculated analytically from the physical dimensions of the coupler, e.g., from a transmission-line model:

$$\begin{pmatrix} p_{ref} \\ U_{ref} \end{pmatrix} = \begin{pmatrix} \cosh(\Gamma L) & -Z_0 \sinh(\Gamma L) \\ -\frac{1}{Z_0} \sinh(\Gamma L) & \cosh(\Gamma L) \end{pmatrix} \cdot \begin{pmatrix} p_{probe} \\ U_{probe} \end{pmatrix}$$

Where $Z_0$ is the characteristic impedance, $\Gamma$ is the propagation constant, L is the length of the transmission line, and $U_{ref}$ is the volume velocity on the reference microphone. Assuming that the coupler is a hard-walled, rigidly terminated waveguide, setting $U_{ref}=0$ and $U_{probe}=1$, $p_{ref}$ can be isolated and interpreted directly as the transfer impedance as a consequence of setting $U_{probe}=1$, i.e., the transfer impedance is given by the following expression:

$$Z_{trans} = Z_0 \frac{\cosh^2(\Gamma L)}{\sinh(\Gamma L)} - Z_0 \sinh(\Gamma L)$$

Normally, the input impedance of the reference microphone $Z_{mic}$ is large enough that it can be neglected, but if the input impedance $Z_{mic}$ of the reference microphone is supplied by the manufacturer it could be included in the model by setting $U_{ref}=p_{ref}/Z_{mic}$ and again solving for $p_{ref}$ resulting in:

$$Z_{trans} = \frac{\cosh(\Gamma L) - \frac{\sinh^2(\Gamma L)}{\cosh(\Gamma L)}}{\frac{1}{Z_{mic}} + \frac{1}{Z_0} \tanh(\Gamma L)}$$

The reference microphone impedance is not included in these investigations since it is not supplied for the used microphone. Brüel & Kjær supplies this information for some microphones and one could imagine a measurement setup, where the inclusion of this parameter could be beneficial.

Figure 4A:
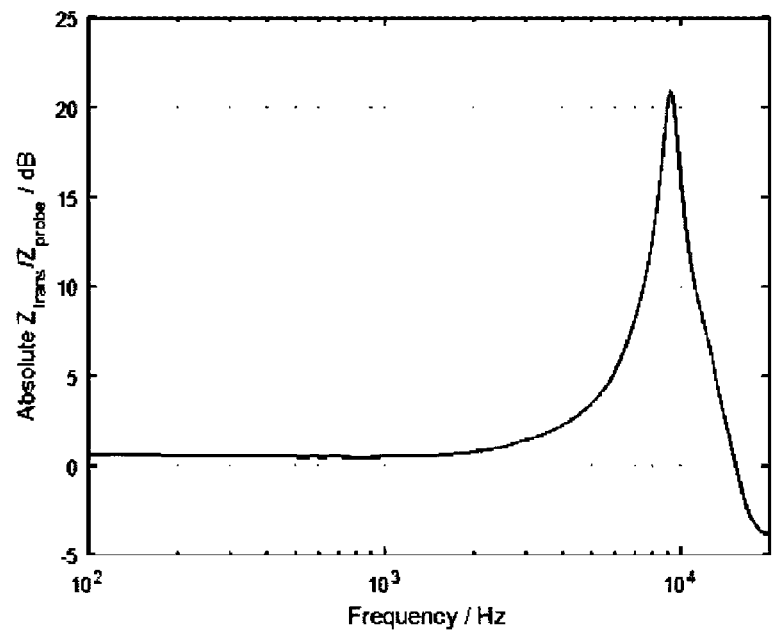
FIG. 4A and FIG. 4B show plots of the magnitude (FIG. 4A) and phase (FIG. 4B) of the transfer-function of the acoustic coupler derived from the ratio between the calculated transfer impedance and the measured input impedance used for calibrating the actual sound pressure at the probe microphone based on the sound pressure at the reference microphone.
Figure 4B:
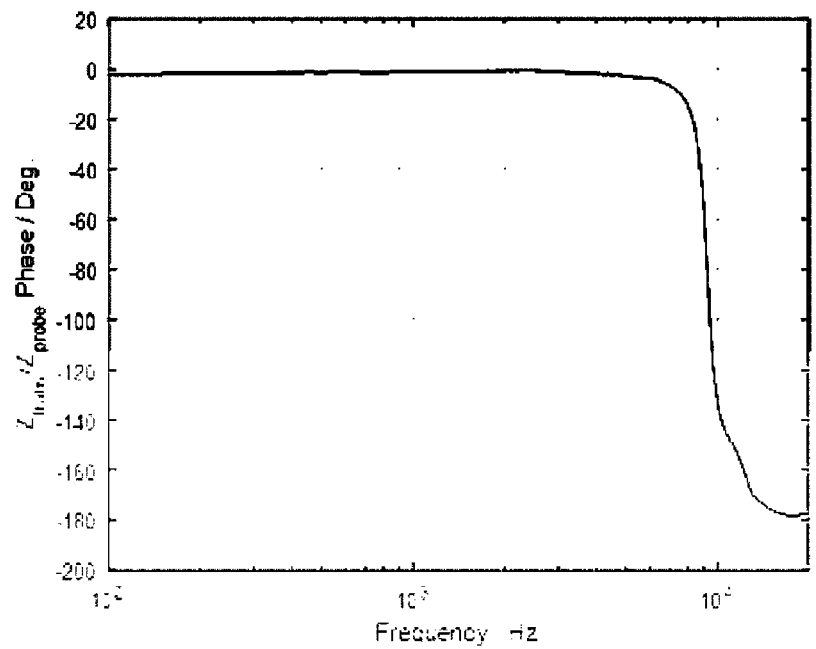

The transfer impedance found by using the physical dimensions of the utilized 0.4 cc coupler is depicted as the last curve 9 in FIGS. 3A and 3B. Having calculated the analytical transfer impedance and measured input impedance, the ratio between these impedances can be calculated. The result is depicted in FIGS. 4A and 4B that shows plots of the magnitude (FIG. 4A) and phase (FIG. 4B) of the ratio between the calculated transfer impedance and the measured input impedance used for calibrating the actual sound pressure at the probe microphone based on the sound pressure at the reference microphone.

The compensated microphone sensitivity can now be determined based on the quantities:
(i) The output voltage $V_{probe}$ (reference numeral 4 in FIG. 1) provided by the probe microphone;
(ii) The sound pressure $p_{ref}$ measured by the reference microphone 6 and provided to a processing unit by line 8;
(iii) The predetermined or simultaneously measured input impedance $Z_{in}$ of the coupler 5; and
(iv) The calculated transfer impedance $Z_{trans}$ that may be analytically calculated for a coupler of comparatively simple geometry.

It should be understood that the method according to the present disclosure could also be utilized using any coupler with a predetermined transfer impedance, which are stored in a processing unit of the equipment, such as a diagnostic tool, used for calibration purposes.

Specifically, the microphone sensitivity can be determined by the following expression:

$$\text{Sensitivity} = \frac{V_{probe}}{p_{probe}} = V_{probe} \cdot \frac{1}{p_{ref}} \cdot \frac{Z_{trans}}{Z_{in}}$$

wherein the output voltage $V_{probe}$ and the reference sound pressure $p_{ref}$ are measured for instance with the setup shown in FIG. 1, $Z_{in}$ has been determined prior to or simultaneously with the measurement, and $Z_{trans}$ has been analytically determined or is known for the specific coupler, for instance as described above.

Figure 5A:
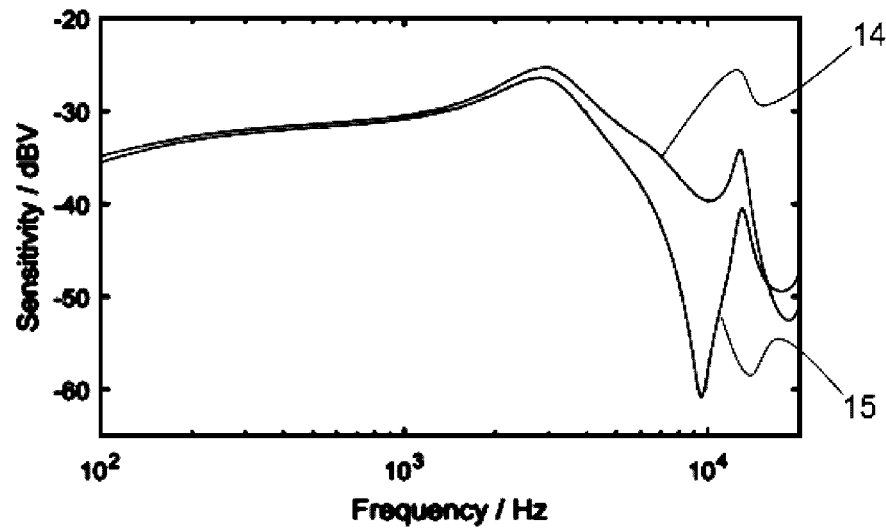
FIG. 5A and FIG. 5B show plots of the magnitude (FIG. 5A) and phase (FIG. 5B) of a non-compensated microphone sensitivity and the corresponding compensated sensitivity obtained by a method according to the present disclosure.
Figure 5B:
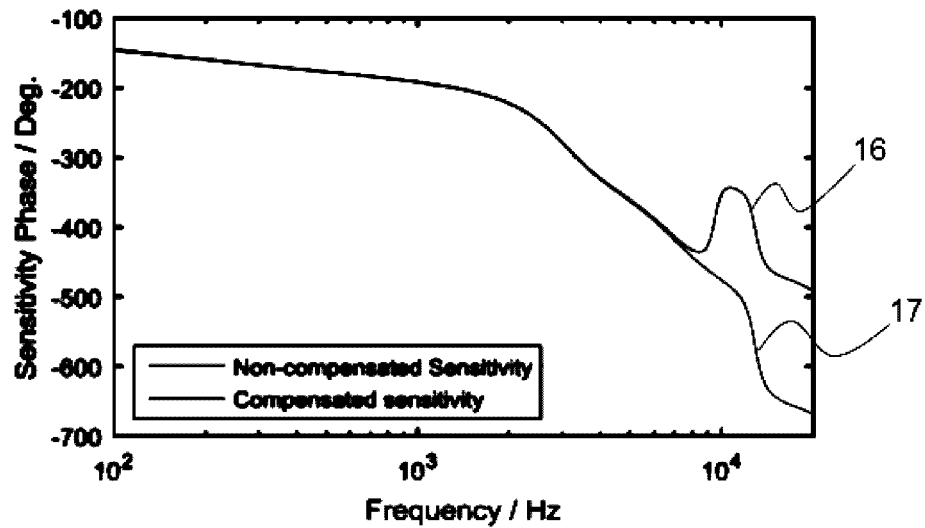

With reference to FIGS. 5A and 5B that show plots of the magnitude (FIG. 5A) and phase (FIG. 5B) of a non-compensated microphone sensitivity (magnitude 15 and phase 16, respectively) and the corresponding compensated sensitivity (magnitude 14 and phase 17, respectively) obtained by a method according to the present disclosure, a compensation of the sensitivity can now be made by multiplying the pressure on the reference microphone by the ratio of impedances in the sensitivity calculation, as given by the above equation of sensitivity.

Figure 6A:
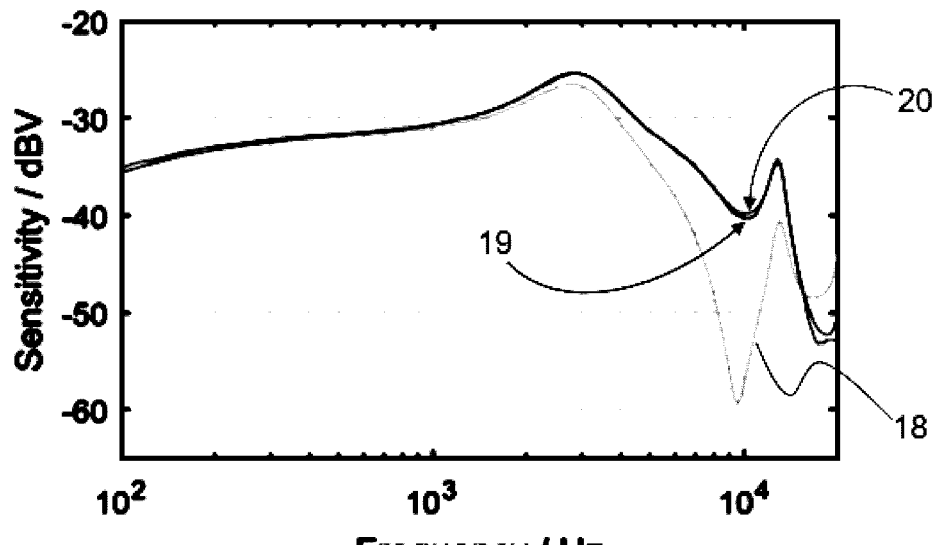
FIG. 6A and FIG. 6B show plots of the magnitude (FIG. 6A) and phase (FIG. 6B) of the free-field sensitivity of the probe microphone compared to the compensated and non-compensated sensitivities of the same probe microphone.
Figure 6B:
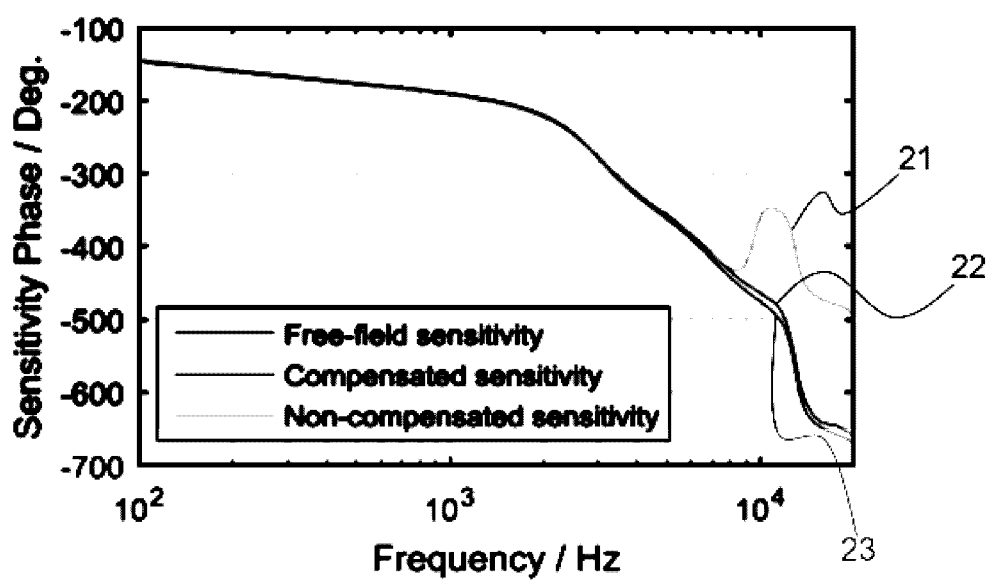

In order to validate the method, the free-field sensitivity of the probe was measured using a sound box with a build-in loudspeaker by placing the reference and probe microphones in close proximity to each other. The result is presented in FIGS. 6A and 6B that shows plots of the magnitude (FIG. 6A) and phase (FIG. 6B) of the free-field sensitivity of the probe microphone compared to the compensated and non-compensated sensitivities of the same probe microphone. Specifically, 18 shows the magnitude of the non-compensated sensitivity, 19 shows the magnitude of the free-field sensitivity and 20 shows the magnitude of the compensated sensitivity obtained with a method according to the present disclosure. Similarly, 21 shows the phase of the non-compensated sensitivity, 22 shows the phase of the free-field sensitivity and 23 shows the phase of the compensated sensitivity obtained with a method according to the present disclosure. It is clear from the FIGS. 6A and 6B that the compensated sensitivity measure substantially follows the curve of the free-field sensitivity measure.

Figure 7A:
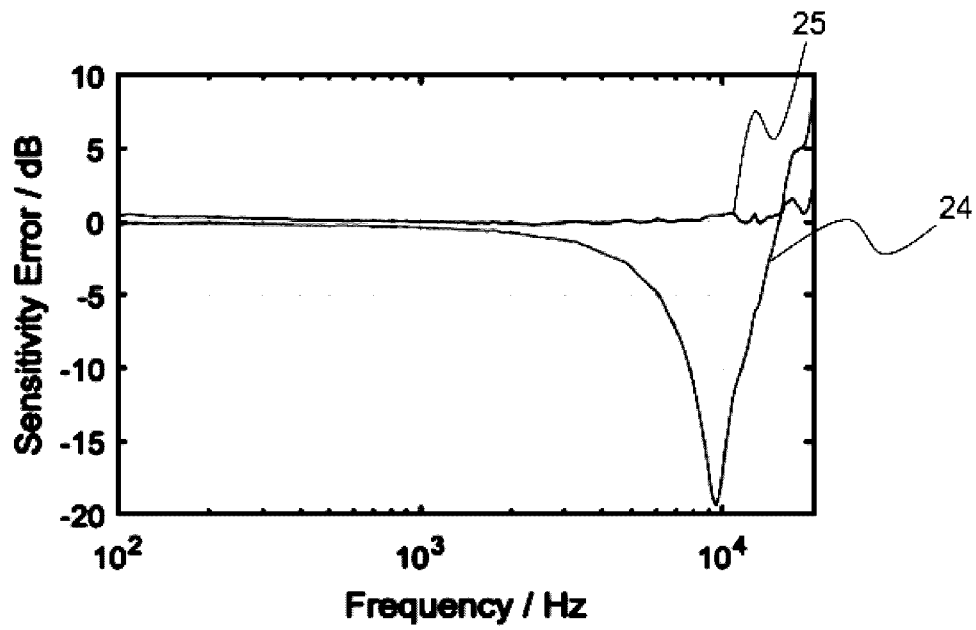
FIG. 7A and FIG. 7B show plots of an example of the magnitude (FIG. 7A) and phase (FIG. 7B) of the error of the compensated and non-compensated sensitivities relative to the corresponding free-field sensitivity.
Figure 7B:
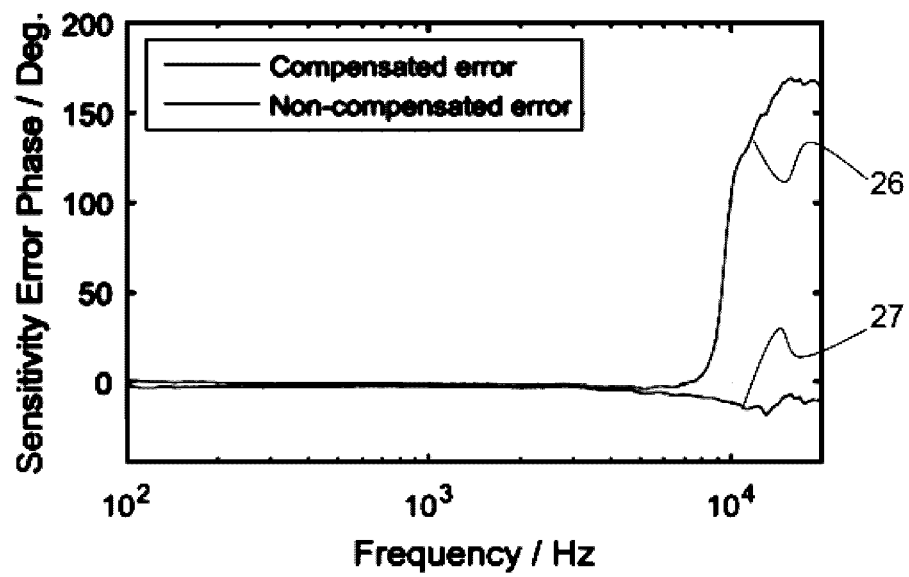

This observation is further confirmed with reference to FIGS. 7A and 7A where plots of an example of the magnitude (FIG. 7A) and phase (FIG. 7B) of the error of the compensated and non-compensated sensitivities relative to the corresponding free-field sensitivity are shown. Reference numeral 24 shows the magnitude error of the non-compensated sensitivity, 25 shows the magnitude of the error of the compensated sensitivity, and 26 and 27 show the corresponding phase of the respective errors. FIGS. 7A and 7B clearly demonstrate the capabilities of the method according to the present disclosure, showing errors that are practically negligible up to frequencies well above 10 kHz.

Figure 8:
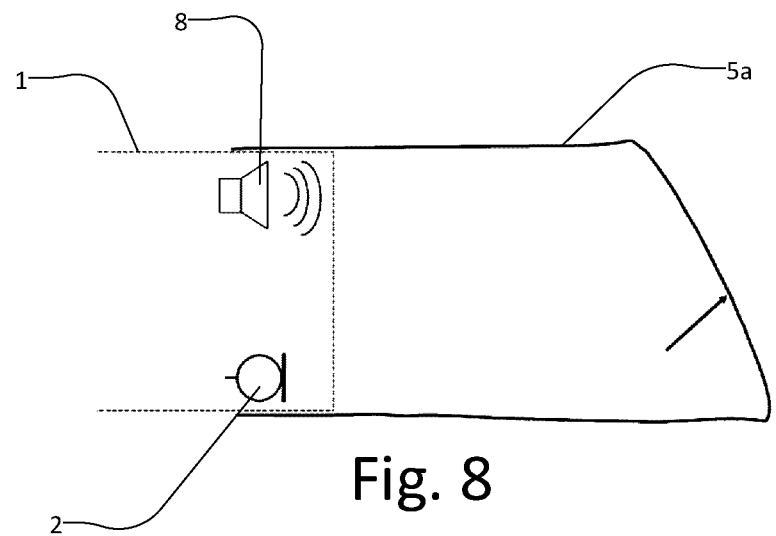
FIG. 8 shows a schematic hearing diagnostic setup.

Referring now to FIG. 8, a simplified hearing diagnostic setup is shown, where an acoustic unit, such as a probe unit 1, is acoustically connected with an acoustic element 5a, in this case illustrated as the ear canal of a human and/or animal test-subject. When performing otoacoustic-emission (OAE) measurements, a speaker unit 8 of the probe unit 1 transmits an acoustic stimulus and/or sound signal into the ear canal of a test-subject. Subsequently the small hair cells of the cochlea of the ear (not shown) reflects a sound signal as a response to the increased sound pressure in the ear canal, which response in OAE measurements are recorded by the microphone 2 of the probe unit 1. As previously explained, it is therefore important that the microphone 2 of the probe unit 1 is able to record a correct and accurate measurement of the response.

Figure 9:
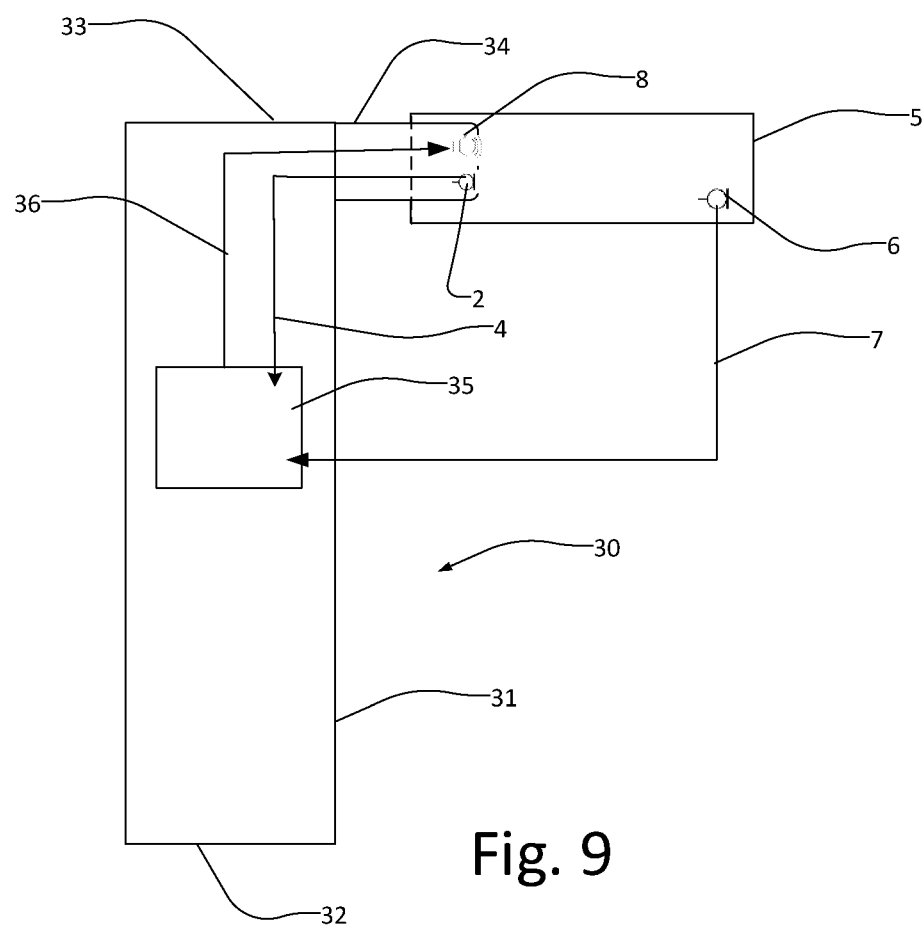
FIG. 9 shows schematically a diagnostic tool used in a hearing diagnostic calibration system setup.

Accordingly, and with reference to FIG. 9, a diagnostic tool, e.g., used for OAE measurements, may be configured to perform a calibration procedure of the microphones, to make sure that the most accurate measurements is recorded for diagnostic purposes. Such diagnostic tool 30 is schematically illustrated in FIG. 9, and comprises a handle element 31 having a first end 32 and a second end 33, wherein an acoustic unit 34 is provided in the second end 33. The acoustic unit 34 (such as a probe unit) comprising at least one output unit 8 (e.g. a receiver) configured to provide a stimulus signal to an acoustic coupler 5 and/or an ear canal 5a, and at least one input unit 2 (e.g., a microphone) configured to record a transmitted sound from inside the acoustic coupler 5, wherein the diagnostic tool 30 further comprises a processing unit 35. As has already been touched upon, the processing unit 35 is configured to perform a calibration procedure of the acoustic unit 34, where the calibration procedure should be understood to include the method described throughout this disclosure.

It should be noted, that the acoustic unit 34 could be directly coupled to the second end 33 of the handle element 31, as shown in FIG. 9. However, in an embodiment and as show in FIG. 10, the acoustic unit 34, such as a probe unit, is instead connected to the handle element 31 on the diagnostic tool 30, such as the second end 33 of the handle element 31, by use of a communication element 37. The communication element 37 is configured to transmit information to and/or from a part of the acoustic unit to the handle element. By partly creating a physical spacing (i.e., through the communication element 37) between at least the acoustic elements 38 (including the microphone 2 and the speaker 8) of the acoustic unit 34 and the handle element 31, potential vibrations or other motional effects introduced by an "operator" or similarly a "user" (e.g., a hearing-care professional) is avoided. Such introduced vibration and/or motional effects from operating the diagnostic tool might lead to the introduction of errors in the measurements performed by the acoustic unit and such errors should preferably be limited as much as possible.

Figure 10:
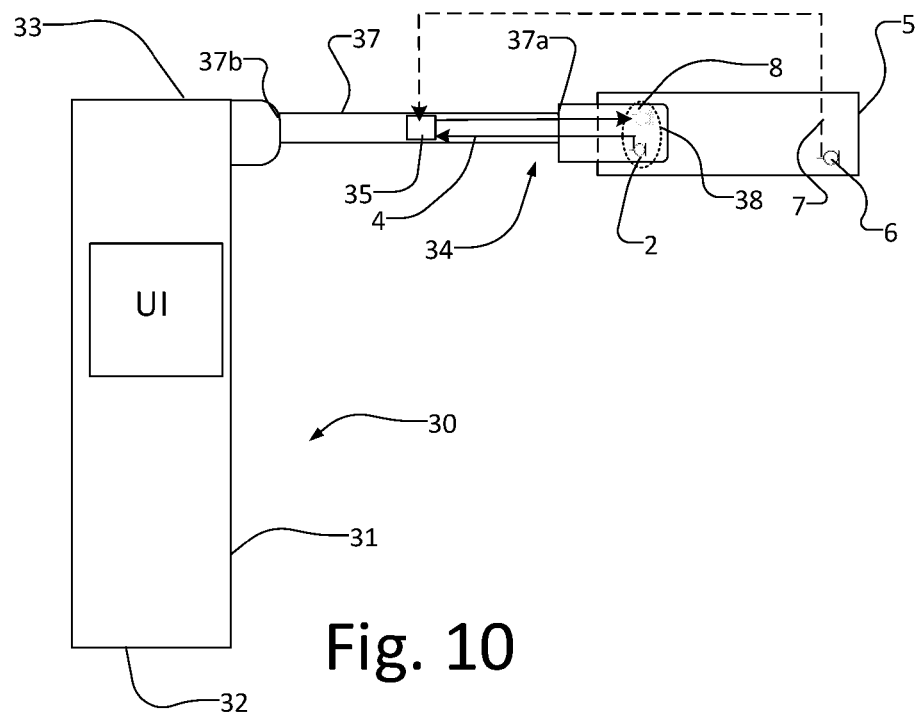
FIG. 10 shows schematically a diagnostic tool used in a hearing diagnostic calibration system, the diagnostic tool having the acoustical elements of the acoustic unit physically separated from the handle element.

Thus, as illustrated in FIG. 10, the acoustic unit may in an embodiment have the acoustical elements 38, such as the input unit (i.e., the microphone) and the receiver arranged in one end 37a of the acoustic unit. The end 37a comprising the acoustical elements 38 is configured to be inserted into an ear canal and/or an acoustic coupler. The other end 37b of the acoustic unit is configured to attach the acoustic unit 34 to the handle element 31 of the diagnostic tool. Accordingly, the second end 37b of the acoustic unit comprises attachment means (not shown) configured to engage with corresponding attachment elements on the handle element 31. As is apparent from FIG. 10, the acoustical elements 38 are connected to the connection end 37b (equally understood to be the second end of the acoustic unit) via the communication element 37. The communication element 37 is configured to transmit information through one or more electrically leading cables and/or wires, which preferably are separated from the environment by an enclosure, such as a tubing (not shown in more detail).

In an embodiment, it may be that the data obtained from the calibration procedure are saved in the acoustic unit 34, rather than in the handle element 31 of the diagnostic tool as such. In this way, the acoustic unit 34 may be interchangeable between different diagnostic tools. In more detail, the acoustic unit 34 is detachable from a handle element 31 of a diagnostic tool, and the calibration data are saved in a processing unit of the acoustic unit 34 rather than in a processing unit of the handle element. Thus, a probe microphone being calibrated according to the method described herein may be used with different diagnostic tools.

Accordingly, and as illustrated in FIG. 10, the acoustic unit 34 may comprise a processing unit 35, which processing unit substantially perform and executes the method described throughout the disclosure.

In both embodiment shown in FIGS. 9 and 10, the handle element of the diagnostic tool may comprise a user interface (denoted UI in FIG. 10), through which an "operator" or similarly a "user" of the diagnostic tool (such as a hearing-care professional) may control, e.g., the calibration procedure described herein.

Furthermore, the handle element of the diagnostic tool may comprise an acoustic coupler entrance, which is configured to connect an electrical leading element of the acoustic coupler used for the calibration purposes, to the handle element, whereby the calibration procedure is be performed directly from the diagnostic tool.

Figure 11:
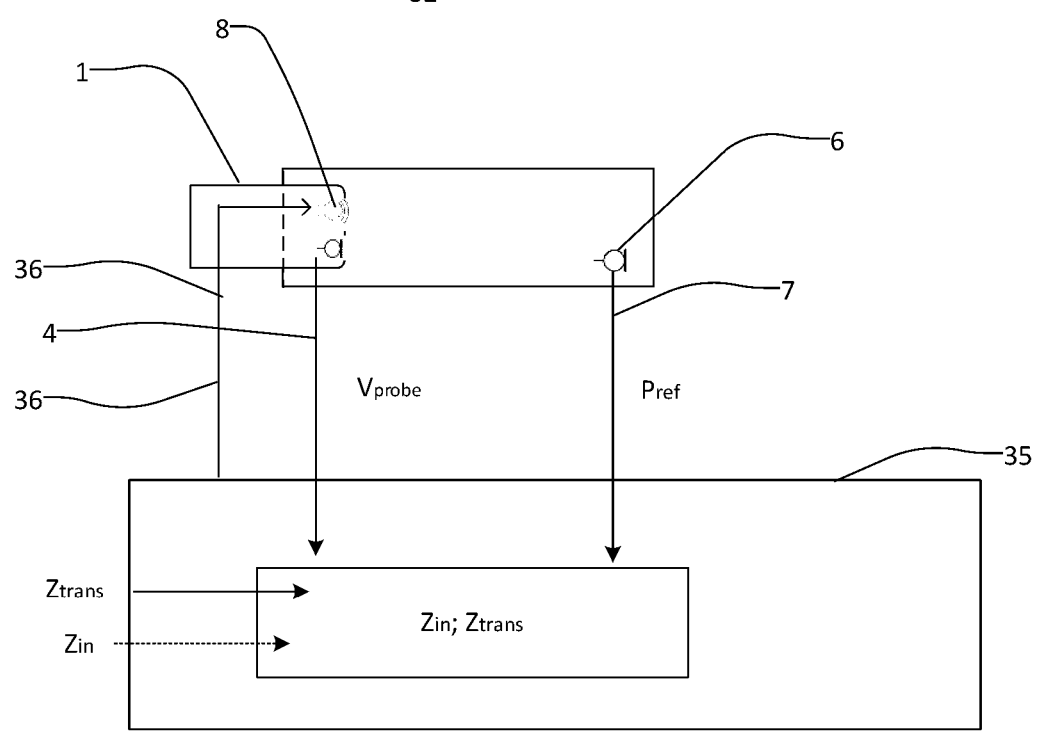
FIG. 11 shows schematically a diagram of the processing unit and the input and output parameters thereof.

In more detail, and with reference to FIGS. 9, 10 and 11, the diagnostic tool 30 is configured so as to control the calibration procedure in a calibration setup of a diagnostic system. That is the processing unit 35 is configured to provide an electrical signal 36 to the sound source 8, whereby the sound source will emit an acoustic stimulus and/or sound signal into the acoustic coupler 5. The processing unit 35 is further configured to receive an electrical output signal 7 from the reference microphone 6 of the acoustic coupler 5. In addition, the processing unit 35 receives a recorded probe microphone signal 4.

The processing unit 35 may store the acoustical parameters characterizing the acoustic behavior of the acoustic coupler for further calibration purposes. The acoustic parameters characterizing the acoustic behavior of the acoustic coupler comprises the input impedance, $Z_{in}$ of the acoustic coupler. The input impedance may be predetermined or measured, as indicated in FIG. 11, by the dotted line $Z_{in}$ and the non-dotted arrow $Z_{in}$, respectively. In addition, stored values of the processing unit comprises any members of the following group or any combinations of these members: recordings or analytical measurements of the system includes; the output voltage, $V_{probe}$ provided by the microphone 2 of the acoustic unit 1, the sound pressure, $p_{ref}$, measured by the reference microphone in the acoustic coupler and the calculated analytical or predetermined transfer impedance $Z_{trans}$ of the acoustic coupler.

As illustrated schematically in FIG. 11, these values, whether predetermined or measured during the calibration procedure is processed in the processing unit, whereby the compensated microphone sensitivity is calculated as previously described.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure.

The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

[1] K. R. Nørgaard, "Correction of analytical impedances in acoustic Thevenin calibration of diagnostic probes and hearing aids, EP application no. 15171935.8.
[2] D. M. Rasetshwane, S. T. Neely, "Calibration of otoacoustic emission probe microphones," J. Acoust. Soc. Am. 130 (4) (2011), JASA Express Letters.

The invention claimed is:

1. A method for determining the sensitivity of a microphone in an acoustic unit, the method comprising:
providing an acoustic unit having a microphone and a sound source;
providing an acoustic coupler having at least one internal cavity configured such that a sound field is generated within the cavity, the cavity being further in acoustic communication with a reference microphone, said reference microphone being configured to measure a reference sound pressure at a given position in said cavity,
establishing acoustic communication between said acoustic coupler and said acoustic unit, in that said cavity is further provided with an opening configured to establish acoustic communication with said acoustic unit;
determining the sensitivity of the acoustic unit, wherein the sensitivity is determined as the ratio between an output voltage of the acoustic unit and said reference sound pressure generated in said cavity by said sound source of said acoustic unit and measured by the reference microphone of the acoustic coupler multiplied by a frequency dependent transfer function, where the transfer function is a function of an input impedance $Z_{in}$ at said opening of the acoustic coupler and a transfer impedance $Z_{trans}$ between the opening of the acoustic coupler and the position at which said reference sound pressure is being measured by the reference microphone.

2. A method according to claim 1, wherein said input impedance $Z_{in}$ at the inlet opening of the acoustic coupler is predetermined or measured.

3. A method according to claim 1, wherein said acoustic unit comprises a microphone unit, the sensitivity of which is measured and compensated for, and the sound source is configured to generate a sound field or sound stimuli in said acoustic coupler, when the acoustic unit is in acoustic communication with the acoustic coupler.

4. A method according to claim 1, wherein said sound source generating a sound field or sound stimuli in the acoustic coupler for measuring the sensitivity of the acoustic unit, is also the sound source that is used for an input impedance measurement.

5. A method according to claim 1, wherein said transfer impedance $Z_{trans}$ is determined analytically in relation to a specific acoustic coupler being used for measuring said sensitivity or measured using other equipment than the acoustic unit.

6. A method according to claim 1, wherein said transfer impedance is calculated analytically based on the physical dimensions of acoustic coupler e.g. from a transmission line model given by:

$$\begin{pmatrix} p_{ref} \\ U_{ref} \end{pmatrix} = \begin{pmatrix} \cosh(\Gamma L) & -Z_0 \sinh(\Gamma L) \\ -\frac{1}{Z_0}\sinh(\Gamma L) & \cosh(\Gamma L) \end{pmatrix} \cdot \begin{pmatrix} p_{probe} \\ U_{probe} \end{pmatrix}$$

where $Z_0$ is the characteristic impedance, $\Gamma$ is the propagation constant, L is the length of the transmission line, $p_{ref}$ is the pressure on the reference microphone of the coupler, $U_{ref}$ is the volume velocity injected into the reference microphone, $p_{probe}$ is the pressure on the acoustic unit (i.e. the microphone unit of the probe unit) and $U_{probe}$ is the volume velocity injected into the acoustic coupler by the acoustic unit.

7. A method according to claim 1, wherein said acoustic coupler is a 0.4 cc (cubic centimeter) acoustic coupler.

8. A method according to claim 1, wherein said acoustic unit is part of an acoustic probe unit configured for use inter alia in hearing diagnostics.

9. A diagnostic tool configured to perform hearing diagnostics and to perform a calibration procedure comprising the method according to claim 1, said diagnostic tool comprising:
a handle element having a first end and a second end, wherein said acoustic unit is provided in said second end;
said acoustic unit comprising at least one output unit configured to provide a stimulus signal to said acoustic coupler, and at least one input unit configured to record a transmitted sound from inside said acoustic coupler, wherein said diagnostic tool further comprises a processing unit, said processing unit being configured to calibrate said acoustic unit by performing said calibration procedure comprising the method according to claim 1.

10. A system for providing hearing diagnostics and for performing a calibration procedure comprising the method according to claim 1, said system comprising:
said acoustic coupler,
a diagnostic tool configured to perform hearing diagnostics, said diagnostic tool comprising;
a handle element having a first end and a second end, wherein said acoustic unit is provided in said second end;
said acoustic unit comprising at least one output unit configured to provide a stimuli signal to said acoustic coupler, and at least one input unit configured to record a transmitted sound from inside said acoustic coupler,
said diagnostic tool further comprising a processing unit, said processing unit being configured to calibrate said acoustic unit, when said diagnostic tool is in acoustic communication with a cavity of said acoustic coupler during calibration procedures, by performing said calibration procedure comprising the method of claim 1.

11. A system according to claim 10, wherein said output unit of the acoustic unit is a speaker unit configured to emit an acoustic stimuli or sound signal into said acoustic coupler, and said input unit/recording unit is a microphone unit configured to measure the resulting sound pressure at an inlet position of the acoustic coupler, wherein said acoustic coupler further comprises a reference microphone configured to measure the sound pressure at an outlet position of said acoustic coupler.

12. A system according to claim 11, wherein said processing unit is configured to provide an electrical signal to said sound source, whereby the sound source emits said acoustic stimuli or sound signal into said acoustic coupler, said processing unit being further configured to receive an electrical output signal from said reference microphone of the acoustic coupler; and said processing unit being configured to store data comprising acoustic parameters characterizing the acoustic behavior of the acoustic coupler.

13. A system according to claim 10, wherein said calibration procedure is configured to calibrate a microphone unit of the acoustic unit.

14. A system according to claim 12, wherein said acoustic parameters characterizing the acoustic behavior of the acoustic coupler comprises the input impedance, $Z_{in}$ of the acoustic coupler, said input impedance being predetermined or measured, wherein stored values of said processing unit comprises one or more of the following: recordings or analytical measurements of the system includes; the output voltage provided by the acoustic unit, the sound pressure measured by the reference microphone, the calculated analytical or predetermined transfer impedance of the acoustic coupler.

15. A system according to claim 10, wherein the processing unit is configured to calculate an analytical transfer impedance of said acoustic coupler from said stored data, and further to output or store said calculated compensated microphone sensitivity values for a specific frequency range.

16. A method according to claim 2, wherein said acoustic unit comprises a microphone unit, the sensitivity of which is to be measured and compensated for, and a sound source configured to generate a sound field or sound stimuli in said acoustic coupler, when the acoustic unit is in acoustic communication with the acoustic coupler.

17. A method according to claim 2, wherein said sound source generating a sound field or sound stimuli in the acoustic coupler for measuring the sensitivity of the acoustic unit, is also the sound source that is used for the input impedance measurement.

18. A method according to claim 3, wherein said sound source generating a sound field or sound stimuli in the acoustic coupler for measuring the sensitivity of the acoustic unit, is also the sound source that is used for the input impedance measurement.

19. A method according to claim 2, wherein said transfer impedance $Z_{trans}$ is determined analytically in relation to a specific acoustic coupler being used for measuring said sensitivity or measured using other equipment than the acoustic unit.

20. A method according to claim 3, wherein said transfer impedance $Z_{trans}$ is determined analytically in relation to a specific acoustic coupler being used for measuring said sensitivity or measured using other equipment than the acoustic unit.

* * * * *